US012661183B2

(12) United States Patent
Ballan et al.

(10) Patent No.: US 12,661,183 B2
(45) Date of Patent: *Jun. 23, 2026

(54) SYSTEM AND METHOD, FOR TRAINING AN INTERVENTIONALIST TO PERFORM AN INVASIVE PERCUTANEOUS INTERVENTION OR AN ENDOSCOPIC INTERVENTION

(71) Applicant: ADIS SA, Lausanne (CH)

(72) Inventors: Hussein Ballan, St-Légier (CH); Pascal Fua, Vaux-sur-Morges (CH); Georges Caron, Echandens (CH); Jürg Schwitter, Lutry (CH); Luigi Bagnato, Lausanne (CH)

(73) Assignee: ADIS SA, Lausanne (CH)

( * ) Notice: Subject to any disclaimer, the term of this patent is extended or adjusted under 35 U.S.C. 154(b) by 1092 days.

This patent is subject to a terminal disclaimer.

(21) Appl. No.: 17/661,111

(22) Filed: Apr. 28, 2022

(65) Prior Publication Data

US 2022/0346878 A1 Nov. 3, 2022

(30) Foreign Application Priority Data

Apr. 29, 2021 (EP) .................................... 21171373

(51) Int. Cl.
| | |
|---|---|
| *A61B 34/10* | (2016.01) |
| *A61B 34/20* | (2016.01) |
| *G06N 20/00* | (2019.01) |
| *G06T 12/00* | (2026.01) |
| *G06T 15/08* | (2011.01) |

(52) U.S. Cl.
CPC .............. *A61B 34/10* (2016.02); *A61B 34/20* (2016.02); *G06N 20/00* (2019.01); *G06T 12/00* (2026.01); *G06T 15/08* (2013.01); *A61B 2034/104* (2016.02); *A61B 2034/105* (2016.02); *A61B 2034/107* (2016.02); *A61B 2034/2055* (2016.02); *G06T 2210/41* (2013.01)

(58) Field of Classification Search
CPC ... A61B 34/10; A61B 34/20; A61B 2034/104; A61B 2034/105; A61B 2034/107; A61B 2034/2055; G06N 20/00; G06T 12/00; G06T 15/08; G06T 2210/41
See application file for complete search history.

(56) References Cited

U.S. PATENT DOCUMENTS

| | | | |
|---|---|---|---|
| 12,402,949 B2 * | 9/2025 | Corazza ................. | G06T 7/251 |
| 2005/0084833 A1 | 4/2005 | Lacey et al. | |
| 2010/0167249 A1 | 7/2010 | Ryan | |

* cited by examiner

*Primary Examiner* — Nirvana Deonauth
(74) *Attorney, Agent, or Firm* — McDonald Hopkins LLC

(57) ABSTRACT

System for training an interventionalist to perform an invasive percutaneous or endoscopic intervention on an organ includes a pipe having a size and/or shape similar to a body vessel or tubular body cavity connected to the organ. An exit of the pipe simulates or represents an exit of the vessel or cavity at the organ. A tool is inserted at an entrance of the pipe and pushed through the pipe. A stereoscopic camera acquires images of an end portion of the tool as it exits from the pipe. A model generating unit generates a real-time 3D model of this end portion from the images. A merging unit merges in real time the real-time model and a pre-computed 3D model of the organ into a common environment displayed so that the interventionalist can see in real-time where the real-time model of the tool is located with respect to the pre-computed model.

15 Claims, 9 Drawing Sheets

500'

=1'

SYSTEM AND METHOD, FOR TRAINING AN INTERVENTIONALIST TO PERFORM AN INVASIVE PERCUTANEOUS INTERVENTION OR AN ENDOSCOPIC INTERVENTION

TECHNICAL DOMAIN

The present invention concerns a system and method, for training an interventionalist to perform an invasive percutaneous intervention or an endoscopic intervention on an organ of a human body or of an animal body ("organ" in the following), using a tool.

RELATED ART

Invasive percutaneous or endoscopic interventions on an organ using a tool are now routinely performed. During such interventions, an interventionalist (i.e. a physician specialized to perform invasive percutaneous or endoscopic interventions) inserts a tool into a body vessel of the patient's circulation or into another tubular system of the patient (for example, genito-urinary tract, trachea and bronchi, or the gastro-intestinal tract) to get access to the target, i.e. the abnormality of the organ to be treated by the tool. Non limitative examples of such tools are catheters and guidewires, or devices like valves, or stents (to open a vessel) or coils to block a vessel (which e.g. supplies a tumor). The tools are substantially filiform. Their diameter is in the order of a few millimeters, typically three. Since body vessels are neither necessarily straight nor linear, those tools are flexible so that they can follow a path in the body vessel that includes torsions or deformations. Therefore, the tools must also be deformable.

During an invasive percutaneous or endoscopic intervention, once the tool has entered the body via a body vessel connected to the organ to be treated in the case of a percutaneous intervention or via a natural body entrance or body tube or tubular body cavity in the case of an endoscopic intervention (e.g. genito-urinal tract, pulmonary system, gastro-intestinal tract), the interventionalist pushes the tool through this vessel or tube until it reaches the organ. Once the tool has entered the organ, the interventionalist uses the tool for treatment, for example by performing an ablation, taking a histological sample, placing a stent or deploying a device or coil. During the intervention, the interventionalist can move and deform the tool inside the organ.

Catheters are commonly used to treat the heart. For example, given state-of-the-art management techniques of patients with acute myocardial infarctions, an increasing portion of them survive this traumatic event. Unfortunately, some patients may develop inhomogeneous scar formations which are associated with malignant arrhythmias and sudden cardiac death.

To prevent this outcome, patients typically undergo electrophysiological testing followed by ablation of "semi-viable" heart scar tissue, also known as conduction channels, using a catheter. These interventions are performed by highly experienced electrophysiologists, but only 40% to 60% of patients are truly healed when treated with current state-of-the-art ablation techniques.

A contributing factor to this low success rate is that there currently exists no efficient training procedure that would allow interventionalists to practice for such invasive percutaneous interventions before actually performing them for real. This unmet need for training capabilities not only applies to heart interventions but also to interventions on other organs. This includes but is not limited to the brain, and angioplasty of many blood vessels, but also to interventions e.g. in the genito-urinary system (prostate and other organs), the pulmonary system or the gastro-intestinal system (liver and other organs).

In the case of electrophysiological interventions, which is an example of an invasive percutaneous intervention, another contributing factor to this low success rate is the limited visualization of the target scar tissue provided by current voltage mapping techniques. Moreover, current voltage mapping techniques only allow for imperfect control of ablation lesion formation.

SHORT DISCLOSURE OF THE INVENTION

An aim of the present invention is the provision of a system and method that overcome the shortcomings and limitations of the state of the art.

Another aim of the invention is the provision of a system and method that allow interventionalists to be trained thoroughly, without risk to patients, and at a low cost, before performing real interventions on actual patients.

Another aim of the invention is the provision of a system and method that allow to reduce the time occupancy of endoscopic intervention rooms by enabling effective pre-intervention planning.

According to the invention, these aims are attained by the object of the attached claims.

The system according to the invention, for training an interventionalist to perform an invasive percutaneous or endoscopic intervention on an organ, by using a tool in this organ, comprises:

a pipe comprising an entrance and an exit and having a size and/or a shape similar to a body vessel or to a tubular body cavity, the body vessel and the tubular body cavity being connected to the organ, wherein the exit of the pipe physically simulates or represents the exit of the vessel or of the tubular body cavity at its junction with the organ;

this tool, arranged to be inserted by the interventionalist at the entrance of the pipe and to be pushed by the interventionalist through the pipe;

at least one stereoscopic camera arranged to acquire images of an end portion of the tool starting from the moment when this end portion starts emerging from the exit of the pipe;

a real-time 3D model generating unit, arranged for generating a real-time 3D model of this end portion of the tool from the images, a merging unit, arranged for merging in real-time in a common environment the real-time 3D model of the tool and a pre-computed 3D model of at least a portion of the organ;

a display for receiving these data to show to the interventionalist this common environment, so that the interventionalist can see in real-time on the display where the real-time 3D model of the tool is located with respect to the pre-computed 3D model of the portion of the organ, thus making the training of the interventionalist possible.

In this context, the term "vessel" indicates not only a blood vessel such as a vein or an artery, for example, it can be any other type of body vessel or a tubular body cavity, such as the urethra or other tubes that don't carry blood.

In this context, the expression "stereoscopic camera" indicates a camera comprising at least two sensors displaced with respect to each other so that they view substantially the same scene but from a different angle, thereby allowing a stereoscopic reconstruction.

In this context, the expression "real-time 3D model of the end portion of the tool" indicates that this 3D model changes over time. These changes can be captured at frame-rate given the images of the "real" (or "physical" or "concrete") tool that are acquired by the stereoscopic camera(s) while the interventionalist moves or deforms it during the simulated intervention. While training the user moves the tool and those images change over time, so that the corresponding 3D model changes as well. In other words, the real-time 3D model of the end portion of the tool is a video-based 3D model or a dynamic, as opposed to static, 3D model. For example, if the interventionalist manipulates the tool to move it or to deform it, then the 3D model, as shown on the display of the system according to the invention, will move or deform itself, respectively, in real-time so as to reproduce the actual tool motion or deformation, respectively, of the "real" tool as seen by the stereoscopic camera(s).

With respect to the known prior art, the invention has the advantage of delivering an immersive training system that will have a dual purpose. First, it will enable interventionalists to practice invasive percutaneous and endoscopic intervention on 3D models of organs for training purposes. Second, in a more operational context, it will help interventionalists to plan interventions before actually performing them.

The system according to the invention will make it possible to optimize the time, accuracy, and success rate of actual interventions. In the same way that flight training simulators cut down on pilot training costs, the system according to the invention will drastically reduce interventional costs by reducing interventional times at all levels through more thorough pre-operative planning.

In one embodiment, the 3D model of the portion of the organ is a static 3D model, meaning that this 3D model does not change over time. In one embodiment, this static 3D model of the portion of the organ is generated by a machine learning-based module that takes as input images from a Magnetic Resonance Imaging scanner, a CT scanner (computed tomography scanner), or any other device able to generate volumetric images of organs. This (first) machine learning-based module will be named in the following "real-time 3D model generating module".

In this context, the expression "machine learning-based module" indicates a module which needs to be trained in order to learn i.e. to progressively improve a performance on a specific task. In a preferred embodiment, the machine learning-based module is an artificial neural network, or network for short. It comprises a set of artificial neurons that are connected to each other to form a weighted directed graph. The neurons receive inputs from other neurons that feed into them, operate on these inputs, and transmit the results to the neurons they feed into. The edge weights denote the influence that a neuron has on those it is connected to and are computed by a process called learning which involves minimizing a loss function.

Although a neural network is a preferred implementation of the machine-based learning module, it could be implemented using other machine learning techniques, for example and in a non-limiting way Gaussian Processes and Decision Forests.

In one embodiment, the system comprises a second machine learning-based module arranged to compute and/or track in real-time a position of the end portion of the tool with regard to the exit of the pipe. This second machine learning-based module will be named in the following "tool tracking module".

In one embodiment, the real-time 3D model generating unit and the merging unit are integrated into a single computing unit, for example to form a single computational pipeline.

In one embodiment, the real-time 3D model generating unit is arranged to take as input the images captured by the stereoscopic camera(s) and to generate a cloud of 3D points, that denote the position of the end portion of the tool with regard to the exit of the pipe.

In one embodiment, the tool tracking module is arranged to take the cloud of 3D points as input and to generate a 3D occupancy grid whose cells contain probabilities of being crossed by the tool. To this end, it can use a deep-learning architecture known as a UNet, that computes a latent representation of the points cloud.

In one preferred embodiment, the real-time 3D model generating unit comprises the tool tracking module. In this embodiment, the tool tracking module is arranged to extract, from the above-mentioned latent representation, the 3D position of several nodes that define the 3D position of the tool's centerline, with regard to the output of the pipe. This 3D position is in general referred as the output of the real-time 3D model generating unit.

In this context, the term "centerline" indicates the central axis of (at least a portion of) the tool, that is modeled as a set of N nodes, and a set of segments or curves linking the points.

In one embodiment, the number of those nodes depends on the length of the tool. For example, the higher the number of nodes, the longer the tool.

In one embodiment, the nodes are markers visible by the image source, which is not necessarily a stereoscopic camera, but can be for example an IRM scanner or a CT scanner.

In one embodiment, the tool tracking module is arranged to extract from this image source, the 3D position of several (visible) markers that defines the 3D position of the tool's centerline, with regard to the output of the pipe.

In one embodiment, the tool tracking module comprises a unit which uses the above-mentioned latent representation, so as to extract the 3D position of centerline nodes (or markers) with regard to the output of the pipe. In one embodiment, this unit is a Multi-Layer-Perceptron (MLP). In another embodiment, it is a (more sophisticated) fully connected architecture, such a ResNet. In yet another embodiment, this unit is a non-machine learning-based unit, arranged so as to execute a standard centreline algorithm extraction for curve fitting.

In one embodiment, the synthetic or pre-computed 3D model of the organ comprises at least one element characterizing a lesion to be operated on.

In one embodiment, the physical pipe contains a gel or a liquid simulating the physical properties of the liquid contained by the real organ, such as blood in the case of a vessel, or urine in the case of the genito-urinary system, or bile in the case of the gastro-intestinal system, or air in the case of the trachea and bronchi, etc.

In one embodiment, the 3D pre-computed model of the organ shown on the display is augmented by targets designating target area(s) of the organ that have been treated and/or that are to be treated. The targets are of different shapes and colours to avoid confusion.

In one embodiment, the merging unit is arranged so as to execute a calibration step that guarantees proper alignment between the exit of the physical pipe from which the tool emerges (as acquired by the stereoscopic cameras) and the entry point into the pre-computed 3D model of the organ.

The present invention concerns also a method for training a interventionalist to an invasive percutaneous or endoscopic intervention on an organ, by using a tool in this organ, comprises:

providing a pipe, this pipe comprising an entrance and an exit and having a size and/or a shape similar to a body vessel or a tubular body cavity, the body vessel or the tubular body cavity being connected to the organ, wherein the exit of the pipe physically simulates or represents the exit of the vessel or of the body cavity at its junction with the organ;

inserting this tool by the interventionalist at the entrance of the pipe and pushing the tool by the interventionalist through the pipe;

acquiring by at least one stereoscopic camera images of an end portion of the tool starting from the moment in which this end portion starts exiting from the exit of the pipe;

generating, by a real-time 3D model generating unit, a real-time 3D model of this end portion of the tool from the images, merging, by a merging unit, in real-time in a common environment the real-time 3D model of the tool and a pre-computed 3D model of at least a portion of the organ;

displaying on a display for receiving those data, this common environment, so that the interventionalist can see in real-time on the display where the real-time 3D model of the tool is located with respect to the pre-computed 3D model of the portion of the organ, thus making the training of the interventionalist possible.

SHORT DESCRIPTION OF THE DRAWINGS

Exemplar embodiments of the invention are disclosed in the description and illustrated by the drawings in which.

EXAMPLES OF EMBODIMENTS OF THE PRESENT INVENTION

Figure 1:
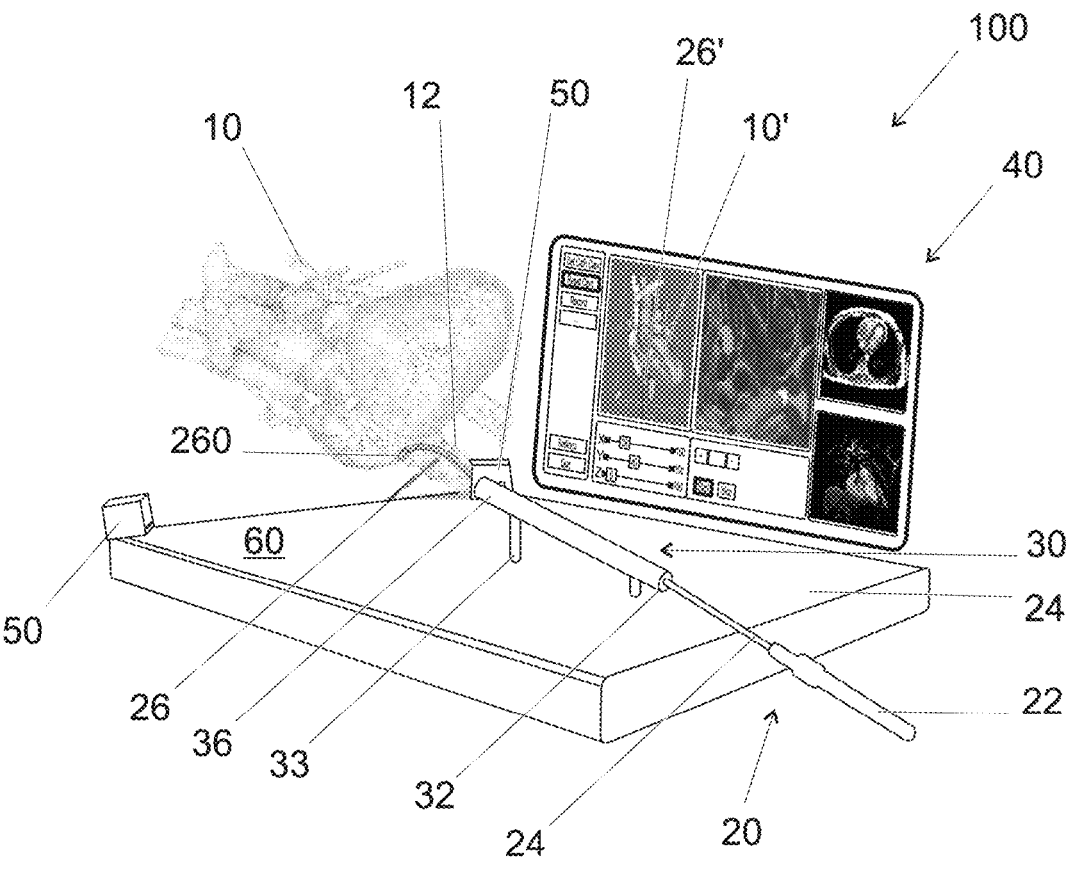
FIG. 1 illustrates a perspective view of one embodiment of the system according to the invention.

FIG. 1 illustrates a perspective view of one embodiment of the system 100 according to the invention. The system

Figure 3:
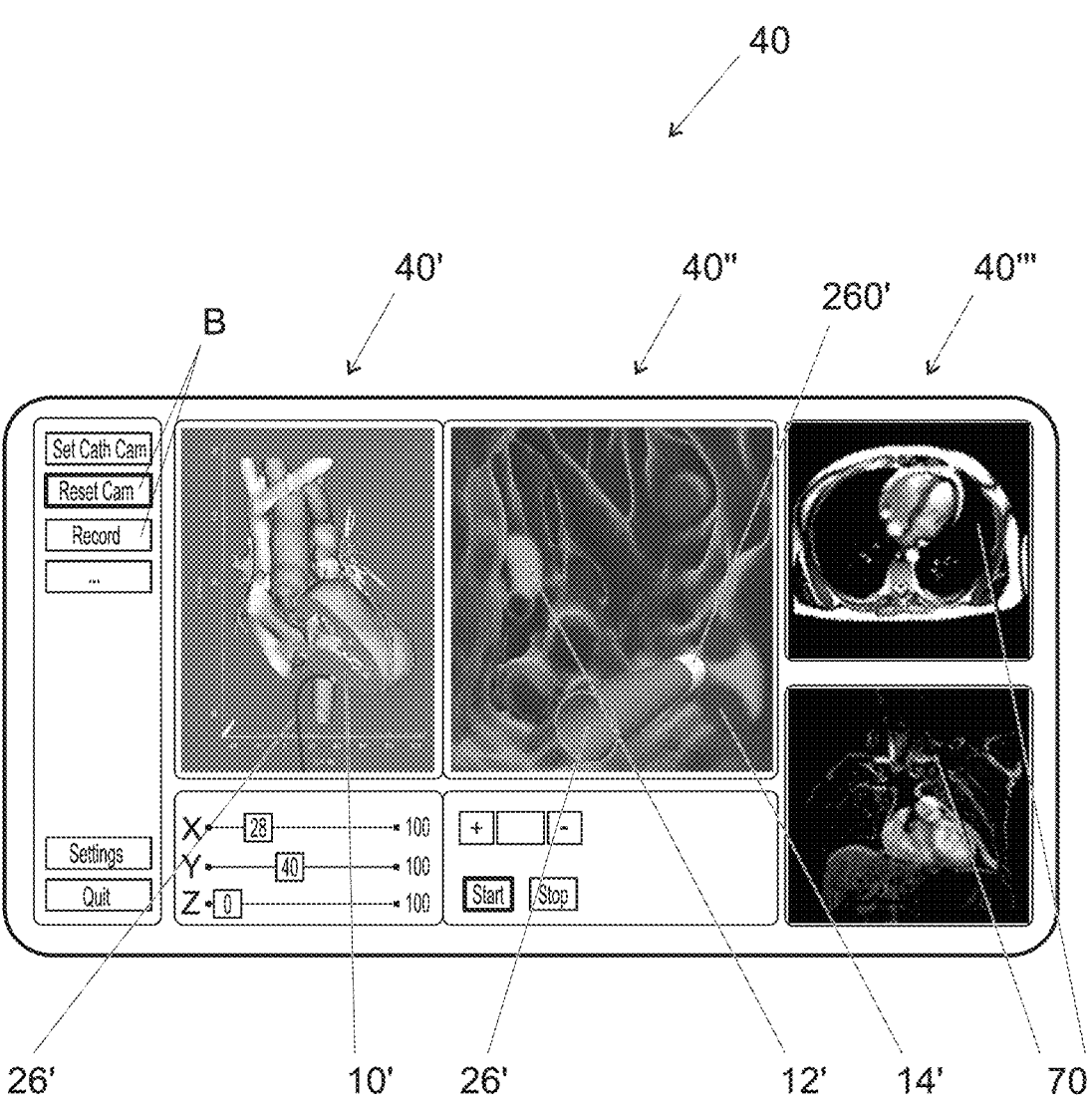
FIG. 3 illustrates a front view of one embodiment of the display of the system according to the invention.

100 can be used to train an interventionalist to perform an invasive percutaneous or endoscopic intervention on a physical organ, by using a tool 20 in the physical organ. The system 100 can also be used for planning interventions. Although FIGS. 1 and 3 depict the 3D model of a heart, the invention could also apply to the entire cardiovascular system (including vessels in any other body part) or other organ systems, such as the genito-urinary system, the pulmonary system, or the gastro-intestinal system and others. While current endoscopic techniques can guide the tool to the organ to treat, the technique as described in this invention not only allows to guide the tool to the organ but once there, it allows to visualize the target even when embedded deeply in the organ and it allows to control the effect of treatment even for targets located deeply in the target organ.

The system 100 of FIG. 1 comprises a:

a pipe 30, a tool 20, such as a catheter in the example of FIG. 1, arranged to be inserted by the interventionalist at the entrance 32 of the pipe 30 through an introducer sheet (not illustrated), which is located at the entrance 32 of the pipe 30, two stereoscopic cameras 50, a real-time 3D model generating unit and a merging unit not shown here, a display 40.

The pipe 30 of the system 100 according to the invention comprises an entrance 32, an exit 36 and a body 33 connecting the entrance 32 with the exit 36. According to the invention, the pipe 30 has a size and/or a shape similar or equal to the size and/or the shape of a vessel connected to the physical organ to be virtually operated on during a training session. In particular, the exit 36 of the pipe 30 simulates or represents the output of the vessel at a junction between the vessel and the organ.

The pipe 30 is intended to simulate a blood vessel, such as a vein or an artery, or any other tubular body cavity, such as the urethra or ureter and others (in the genito-urinary tract), trachea and bronchi (in the pulmonary system), or the bile ducts and others (in the gastro-intestinal tract), through which an interventionalist can access to the organ to be treated using the tool 20.

In one embodiment, the pipe 30 is transparent, so that the interventionalist can see the movement of the tool 20 inside the pipe 30.

In one embodiment, the pipe 30 is made of a polymeric material, or of any other material presenting mechanical characteristics similar or equal to the mechanical characteristics of the corresponding physical vessel.

In one embodiment, the system comprises two or more pipes 30, connected to each other so as to form a ramified arrangement. This allows to simulate a ramified vessel, as one artery or vein separating into two.

In one embodiment, the diameter of the pipe 30 is similar or equal to the diameter of the corresponding physical vessel or other tubular body cavities.

In one embodiment, the length of the pipe 30 is similar or equal to the corresponding length of the vessel. In another embodiment, the pipe 30 is shorter than the corresponding physical vessel.

In one preferred embodiment, the pipe 30 is shorter than the tool 20, without its handle 22.

In one embodiment, the pipe 30 contains a gel or a liquid simulating the physical properties of the liquid contained by the real vessel in the body, such as blood or urine. In one preferred embodiment, this substance is or comprises silicone. Hence, interventionalists will receive the received the same haptic feedback when moving the tool 20 in the pipe 30, as if they were doing it in a real body.

In the example of FIG. 1, the pipe 30 is supported by two feet 33 on a (substantially planar) base 60. However, the feet are not necessary. Moreover, only one foot can be present, as long as the stability of the pipe 30 on the base 60 is not compromised. The feet 33 of FIG. 1 have different heights, so that the pipe 30 is tilted with regards to the planar base 60. Since the system 100 illustrated in FIG. 1 comprises two stereoscopic cameras 50 on the base 60, which are equidistant from the output 32 of the pipe 30, this prevents having a dead angle when the stereoscopic cameras 50 acquire images of a portion of the tool 20, starting from the moment when it exits from the exit 36 of the pipe 30.

In another embodiment that is not illustrated, the system 100 comprises two stereoscopic cameras 50 on the base 60. They are equidistant from the exit 36 of the pipe 30, as the two stereoscopic cameras 50 of FIG. 1, and the pipe 30 lies on the base 60 or in a plane parallel to the base 60. This configuration guarantees that the epipolar lines of the two stereoscopic cameras will not be parallel and will eliminate any potential dead angles.

In another embodiment that is not illustrated, the pipe 30 lies on the base 60 or in a plane parallel to this base 60 and the system 100 comprises two stereoscopic cameras 50 on the base 60, which are equidistant from the exit 36 of the pipe 30, as the two stereoscopic cameras 50 of FIG. 1, and a third camera over the pipe 30 and forming with the exit 36 of the pipe 30 and the other two cameras a tetrahedron. This will be even more effective than the arrangement of 0043 at eliminating any potential dead angles.

Although in FIG. 1 there are two stereoscopic cameras 50, only one is required for the system 100 according to the invention to operate.

In the example of FIG. 1, the tool 20 is a catheter. However, the tool 20 of the system 100 according to the invention can also be any other tool arranged to be inserted by the interventionalist at the entrance 32 of the vessel, so as to reach the organ. For example, and in a non-limiting way, the tool 20 can be a guidewire.

The tool 20 of FIG. 1 comprises a handle 22 arranged to be held by the interventionalist, so as to manipulate the tool 20, and, in particular, to insert it at the entrance of the pipe 30 and to push it through the pipe 30. It also comprises an end portion 26 and a body 24 between the handle 22 and the end portion 26. The end portion 26 comprises a free end 260.

In the illustrated example, the handle 22 has different diameters and its lowest possible diameter is smaller than the diameter of the main body 24 and of the end portion 26. In the illustrated example, the diameter of the main body 24 is equal to the diameter of the end portion 26. However, in other embodiments, those diameters can be different. For example, the diameter of the main body 24 can be smaller than the diameter of the end portion 26.

In one preferred embodiment, the tool 20 without its handle is longer than the pipe 30. Therefore, once the end portion 26 has been inserted at the entrance 32 of the pipe 30 and pushed by the interventionalist toward its exit 36, the free end 260 and then the end portion 26 of the tool 20 will eventually emerge from the exit 36 of pipe 30.

The flexible tool 20 is substantially filiform. The diameters of the main body 24 and of the free end 26 are in the order of few millimeters, typically three millimeters. The tool 20 is flexible. It can be deformed, bended or twisted, so as to follow the shape of the body vessel, or the tubular body cavity and/or of the organ. For example, the end portion 26 of FIG. 1 is curved, so as to follow a curved path in the virtual organ 10.

The system 100 according to the invention also comprises a real-time 3D model generating unit, not illustrated in FIG. 1. It is a computing unit designed to generate in real-time a 3D model of the terminal portion of the tool 20 starting from the time when it emerges from the exit 36 of the pipe 30 given the images acquired by the stereoscopic camera(s) 50, as the interventionalist deforms it during the simulated intervention. In other words, the real-time 3D model of the end portion 26 of the tool is a video-based 3D model or a dynamic, as opposed to static, 3D model.

In a preferred embodiment, the real-time 3D model generating unit comprises a real-time 3D model generating module, which is a machine learning-based module, i.e. a module that needs to be trained in order to progressively improve its performance on a specific task.

In a preferred embodiment, the real-time 3D model generating module is an artificial neural network, or network for short. Although a neural network is a preferred implementation of the machine-based learning module, the real-time 3D model generating module could be implemented using other machine learning techniques that can regress the 3D position of center line nodes of the flexible tool 20 from the output of the stereoscopic camera(s) 50. These include but are not limited to Gaussian Processes and Decision Forests.

In another embodiment, the real-time 3D model generating unit comprises no machine learning-based module. Instead, it is arranged so as to execute curve fitting algorithms.

The real-time 3D model of the end portion 26 of tool 20 changes over time, as it depends on the images taken in real-time of the "real" (or "physical" or "concrete") tool 20, as seen by the stereoscopic camera(s) 50. As the user moves the tool 20 in space so as to virtually treat the body organ, those images change over time and the corresponding 3D model changes as well. In other words, the real-time 3D model of the end portion 26 of the tool 20 is a video-based 3D model or a dynamic 3D model, as opposed to a static one.

The real-time 3D model generating unit is connected to the stereoscopic camera(s) 50. The connection can be wired or wireless. It can be via internet, WLAN, mobile phone network, or any other wireless communication protocols and/or other communication techniques.

In one preferred embodiment, the real-time 3D model generating unit is a device distinct from the other devices of the system 100. However, in one embodiment, it could be, at least partially, be integrated in one of the other devices of the system 100, for example in the display 40 or in a stereoscopic camera 50.

In another embodiment, the real-time 3D model generating unit is at least partially integrated in a remote server.

The system 100 according to the invention also comprises a merging unit that is not illustrated. It a computing unit designed to merge in real-time into a common environment the changing real-time 3D model 26 of the tool 20 and a pre-computed 3D model of at least a portion of the target organ. It outputs the data representing this common environment.

The merging unit can be connected to the real-time 3D model generating unit, so as to form a computational pipeline. The connection can be wired or wireless. It can be via internet, WLAN, mobile phone network, or any other wireless communication protocols and/or other communication techniques.

In one preferred embodiment, the merging unit is a device distinct from the other devices of the system 100. However, in one embodiment, it could be, at least partially, integrated in one of the other devices of system 100, such as in the real-time 3D model generating unit, in the display 40, or in a stereoscopic camera 50.

In another embodiment, the merging unit is at least partially integrated in a remote server.

In one embodiment, the 3D model of the portion of the organ is a static 3D model, meaning that this 3D model does not change over time. In one embodiment, this static 3D model of the portion of the organ is generated by a machine learning-based module, named in the following "static 3D model generating module", that takes as input images from a Magnetic Resonance Imaging scanner, a CT scanner, or any other device able to generate volumetric images of organs.

In one embodiment, the 3D model of the portion of the organ is not static. In the real patient, many organs such as the heart move predominantly in feet-head direction during breathing. To simulate the respiratory motion of portion of the organ within the patient in the system 100, a feet-head motion can be added to the 3D model of the portion of the organ. This feet-head motion can follow simple sinus function, more complex functions, or can use respiratory motion patterns of a specific patient.

The static 3D model generating module can belong to a computing unit of the system 100, or to an external computing unit connected to the system 100.

In one preferred embodiment, the 3D model of at least a portion of the organ is "virtual" as it is not generated by analysing in real-time images of the "real" organ. In other words, the "real" organ is not present in the system 100 according to the invention. In fact, the organ 10 depicted as a heart in FIG. 1 is there for illustration purposes only. The interventionalist cannot see it when looking for example at the end portion 36 of the pipe 30. The interventionalist can only see the corresponding 3D (static) model 10' when looking at the display 40. On the display 40, the interventionalist can also see the real-time 3D model 26' of the end portion 26 of the linear tool 26, this real-time 3D model 26' being displayed in the 3D model 10' of (a portion of) the organ 10.

In fact, according to the invention, the merging unit is arranged to merge in a common environment both the real-time 3D model 26' and the static 3D model 10'. Moreover, the display 40 is arranged for receiving those data in order to display this common environment, so that the interventionalist sees on the display 40 the real-time 3D model 26' of the end portion 26 of the linear tool 20, which is displayed as placed in the (virtual) 3D model 10' of the portion of the organ 10, thus allowing the training of the interventionalist.

The displayed real-time 3D model 26' moves in the (virtual) 3D model 10' according to the movements of the real terminal or end portion 26 of the linear tool 20 as handled by the interventionalist. During the training, the interventionalist looks at the display 40, so as to learn and understand how to move the tool 20 so as to treat the organ.

In one preferred embodiment, the merging unit, before merging in the common environment both the real-time 3D model 26' and the (virtual) 3D model 10', performs a calibration step so as to align the position of an end 360 of the pipe 30, with the position of an entry portion of the (virtual) 3D model. In other words, the exit 36 of the pipe 30, which physically simulates or represents the end of the (real) body vessel (or of the real tubular body cavity) before it enters in the organ, is considered as a reference: the position of the free end 260 of the tool 20 as seen by the stereoscopic camera(s) is computed with regard to that reference.

Figure 2:
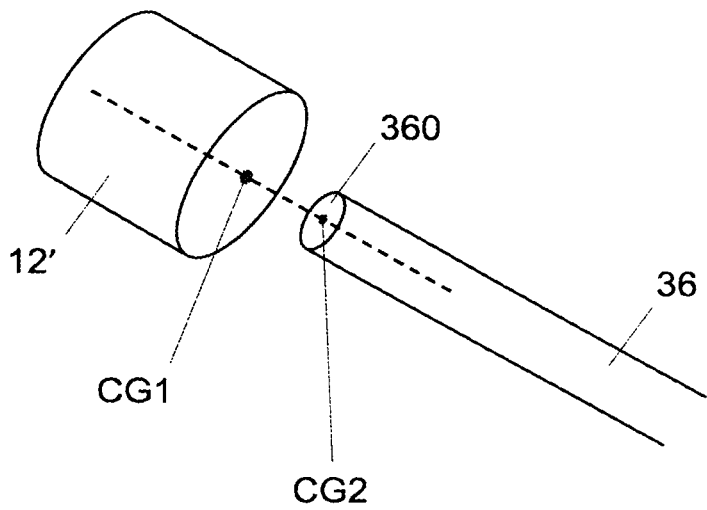
FIG. 2 illustrates a perspective view of a 3D model of an entry portion into the organ and of a 3D model of an end portion of the tool, so as to show the outcome of the calibration step according to one embodiment of the invention.

The entry portion 12 of the (real) organ, which is the portion connected to the (real) body vessel (or to the tubular body cavity), has in general a cylindrical or cylindroidical shape, as illustrated in FIG. 1. The 3D model 12' of this portion has been schematically illustrated also in FIG. 2, along with the exit 36 of the pipe. For sake of simplicity, in FIG. 2 the end portion of the pipe 30 has been represented as a cylinder. In FIG. 2, the end portion 36 is spatially separated from the entry portion 12' for clarity reasons only. During the calibration step, if the entry portion 12' has a cylindrical shape as in FIG. 2, this cylinder is cut by a plane parallel to its base, so as to find the center of geometry CG1 of the cut section. Then, this point is aligned and superposed with a previously computed center of geometry CG2 of the end 360 of the exit 36 of the pipe 30. In this context, the center of geometry (or geometric center or centroid) of a plane figure as the mentioned cut section, is the arithmetic mean position of all the points in the figure.

If the entry portion 12' has a cylindroidical shape, then during the calibration step this cylindroid is cut with two differently inclined planes, so as to find the center of geometry of a first cut section and the center of gravity of the second cut section. Those centers are then aligned between them, so as to find the point to be aligned and superposed to a previously computed center of geometry or the center of gravity CG2 of the end 360 of the pipe 30. In this context, the center of gravity (corresponding in this context to the center of mass, as the gravitational field in which the object exists is assumed to be uniform) is the arithmetic mean of all points weighted by a local density or specific weight. If a physical object has uniform density, its center of mass is the same as the centroid of its shape FIG. 3 illustrates a front view of one embodiment of the display 40 of the system 100 according to the invention. In one preferred embodiment, the display 40 of the system 100 according to the invention is a touch display. In the illustrated embodiment, the display 40 comprises an interventionalist interface, with some (touch) buttons B that can be activated by the interventionalist, e.g. for displaying cut sections of the displayed 3D models, changing the perspective, zooming, etc.

In the embodiment of FIG. 3, the display 40 comprises also three main zones, i.e. a first zone 40', wherein the interventionalist can see the real-time 3D model 26' of the end portion 26 of the tool 20 in the (virtual) 3D model 10' of the organ, a heart in the illustrated example. By moving or manipulating the (real) tool 20, the corresponding 3D model moves on the (first zone 40' of the) display, so that the interventionalist can see how its end portion is placed in the 3D model 10' of the organ.

In the illustrated second zone 40", the interventionalist sees a (perspective) view of the 3D model of the end portion 26' and of the free end 260'. In one preferred embodiment, the interventionalist can see also with a first color the 3D model of the zone(s) 14' inside the organ to be treated and with a second color the 3D model of the zone(s) 16' inside the organ already treated by the 3D model of the free end 260'. In fact, in one preferred embodiment, the virtual 3D model comprises at least one element characterizing a lesion to be operated, as the conduction channel or the scars in the heart. In other words, the 3D pre-computed model 10' of the organ shown on the display 40 is augmented by targets designating target area(s) of the organ that have been treated and/or that are to be treated. The targets are of different shapes and colours to avoid confusion.

In the third zone 40''', the interventionalist can see some images from an IRM scanner or from a CT scanner of the organ. These images can be still frames representing ana- tomical images of the organ or images of electrocardiograms or cine loops (consisting of many images depicting e.g. the contraction of the heart or an electrocardiogram over time). These images and cine loops can be loaded from an external archive, where distinct positions of the 3D pre-computed model 10' of the organ can be linked to specific images or cine loops. The images or cine loops can also be acquired during the intervention and can be directly loaded into the display 40 for visualization. With the images, the interven- tionalist can control the effect of his treatment or he can check the status of the patient in case complications are simulated on the system 100.

The ordering of the three zones of the display 40 of FIG. 3 is not important. Moreover, the second and third zones 40", 40''' are not necessary for the working of the system.

Figure 4:
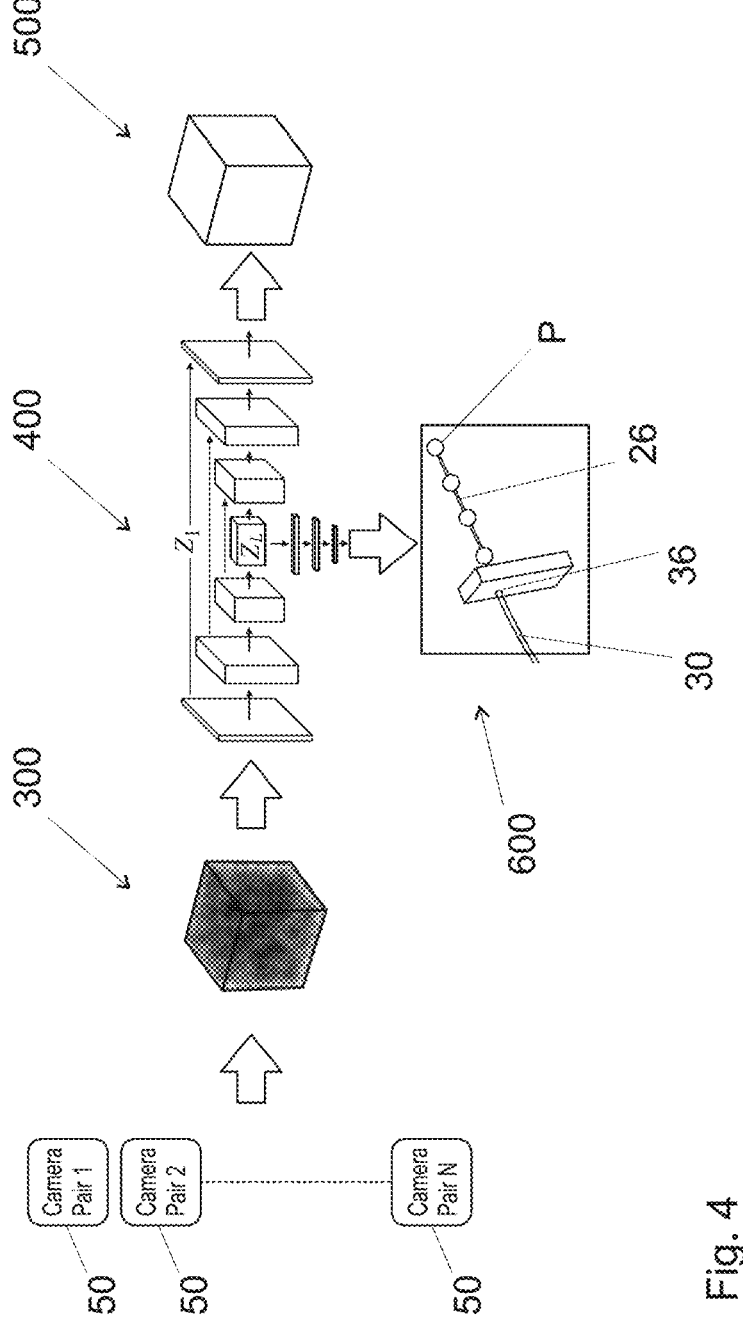
FIG. 4 is a schematic flowchart showing some steps of one embodiment of the method according to the invention.

FIG. 4 is a schematic flowchart showing some steps of one embodiment of the method according to the invention.

The tool 20 is located in a pipe 30 and observed by one or more stereoscopic cameras 50 (N in the example of FIG. 4). The real-time 3D model generating unit is arranged to generate a cloud of 3D points in a grid 300, that denote the position of the tool 20, in particular, the position with regard to the exit 36 of the pipe 30.

In the example of FIG. 4, this cloud of 3D points is fed to a tool tracking module 400, which is a machine learning- based module, such as a neural network, that outputs a grid of probabilities that the tool's centerline crosses the corre- sponding grid cells. That probability grid can then be thresholded to produce the binary occupancy grid 500, with ones where the tool 20 is and zero elsewhere. The same network also outputs the 3D real-world coordinates of 3D points 600. These 3D points define the 3D position of the centerline of the tool 20, with regard to the exit 36 of the pipe 30.

At least a portion of the tool 20 is modeled as a set of N nodes or points P, and a set of segments or curves linking the points. In one preferred embodiment N is an integer number equal or higher than two. In one preferred embodiment, N=4, as illustrated in FIG. 4. Setting N=4 allows to represent a (end) portion of the tool 20, this portion being 6 cm to 10 cm long. In one embodiment, the number of those nodes depends on the length of the tool. For example, the higher the number of nodes, the longer the tool.

In other words, the tool tracking module 400 of FIG. 4 produces a latent representation that is decoded into an occupancy grid 500. The position of the 3D nodes that define the 3D position of the tool's centerline is inferred from this latent representation (reference 600 in FIG. 6).

Figure 5:
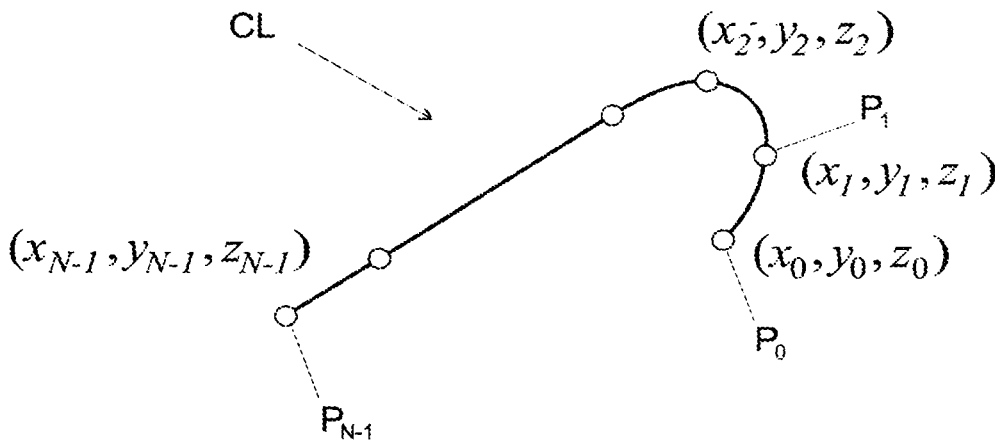
FIG. 5 is a schematic representation of the centerline of one embodiment of an end portion of a tool of the system according to the invention.

FIG. 5 is a schematic representation of the centerline CL of one embodiment of an end portion 26 of a tool 20 of the system according to the invention. The circles depict the aforementioned nodes that define the position of the tool's centerline CL. In one embodiment, the system 100 com- prises a tool tracking module, which is a machine learning- based module arranged to compute and/or track in real-time a position of the tool with regard to the exit 36 of the pipe 30.

In one embodiment, this tool tracking module belongs to the real-time 3D model generating unit. In another embodi- ment it belongs to another computing unit.

In one embodiment, this tool tracking module is arranged to detect the deformation and/or the torsion of the tool 20.

In one preferred embodiment, the tool tracking module is a deep neural network that learns an occupancy map and nodes or point P of the centerline CL belonging to a tool 20. In the example of FIG. 5, the number of points $P_i$ is N, wherein N=0, 1, . . . , N–1. In one preferred embodiment, the point $P_0$, having the coordinates $(x_0, y_0, z_0)$, is the reference point for the system coordinates of the other points. In one preferred embodiment, the point $P_0$ belongs to the exit (surface) 36 of the pipe 30.

Figure 6:
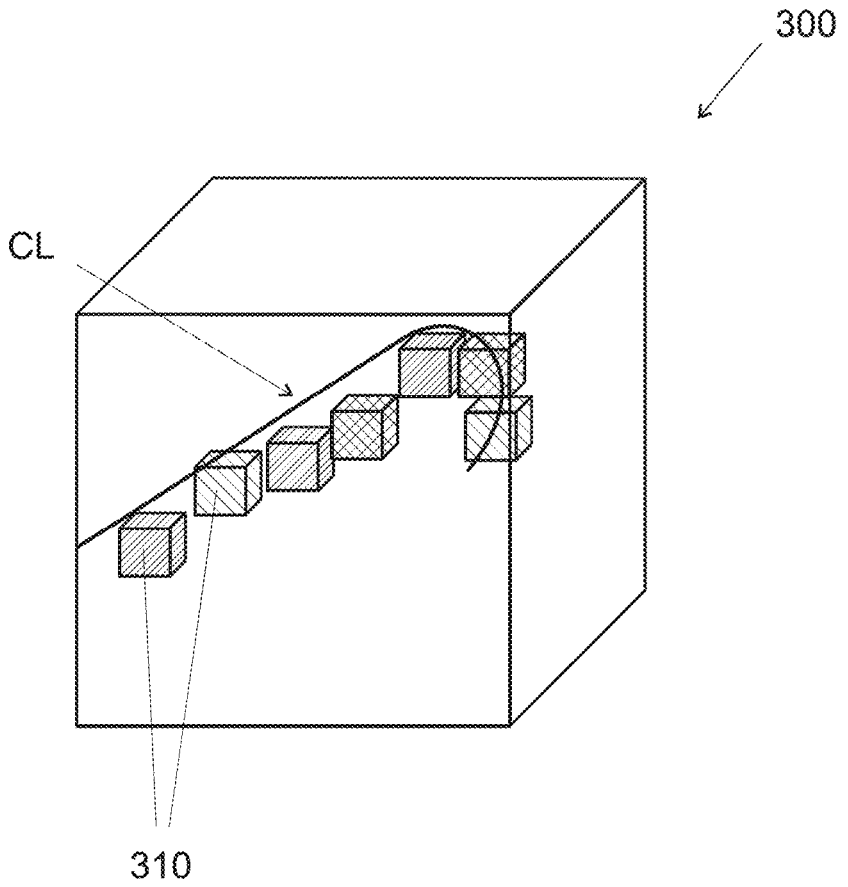
FIG. 6 illustrates an example of the occupancy grid that can be produced according to one embodiment of the method according to the invention.

FIG. 6 is a volumetric discrete representation 300 of the tool 20 represented by a centerline CL in FIG. 4. Although a cube has been illustrated in FIG. 6, other types of volumes are possible, such as parallelepipeds among others.

The volumetric discrete representation 300 of FIG. 6 comprises features map elements 310: those represented in FIG. 6 correspond to the presence of (a portion of the) tool 20 in that sub-volume in the volumetric discrete represen- tation 300. Although (small) cubes have been illustrated in FIG. 6 for representing features map elements 310, other volume types are possible, such as parallelepipeds among others. In general, the shape of the volumetric discrete representation 300 correspond to the shape of the features map elements 310.

The cubes of FIG. 6 exhibit different patterns, denoting different probabilities that the tool 20 cross a particular cube, or different numbers of 3D points within different cubes. Ideally, the predicted centerline CL should go through the part of the volumetric discrete representation 300 where many 3D points have been found.

The deep neural network is arranged to learn from a (manually annotated) volumetric discrete representation of the tool 20 as in the FIG. 6. The volume of data volumetric discrete representation 300 is obtained from at least one stereoscopic camera 50. In one embodiment, stereoscopic camera(s) 50 output disparity maps that are converted into clouds of 3D points and used to compute a 3D point count grid in which the number of points within each grid cell is recorded, as for example illustrated in FIG. 6. This grid is fed as input to a tool tracking module 400 that then outputs a description of the tool 20 in terms of a number of control points linked by a spline curve. In one embodiment, the tool tracking module 400 is a deep neuronal network trained on manually annotated data.

Figure 7:
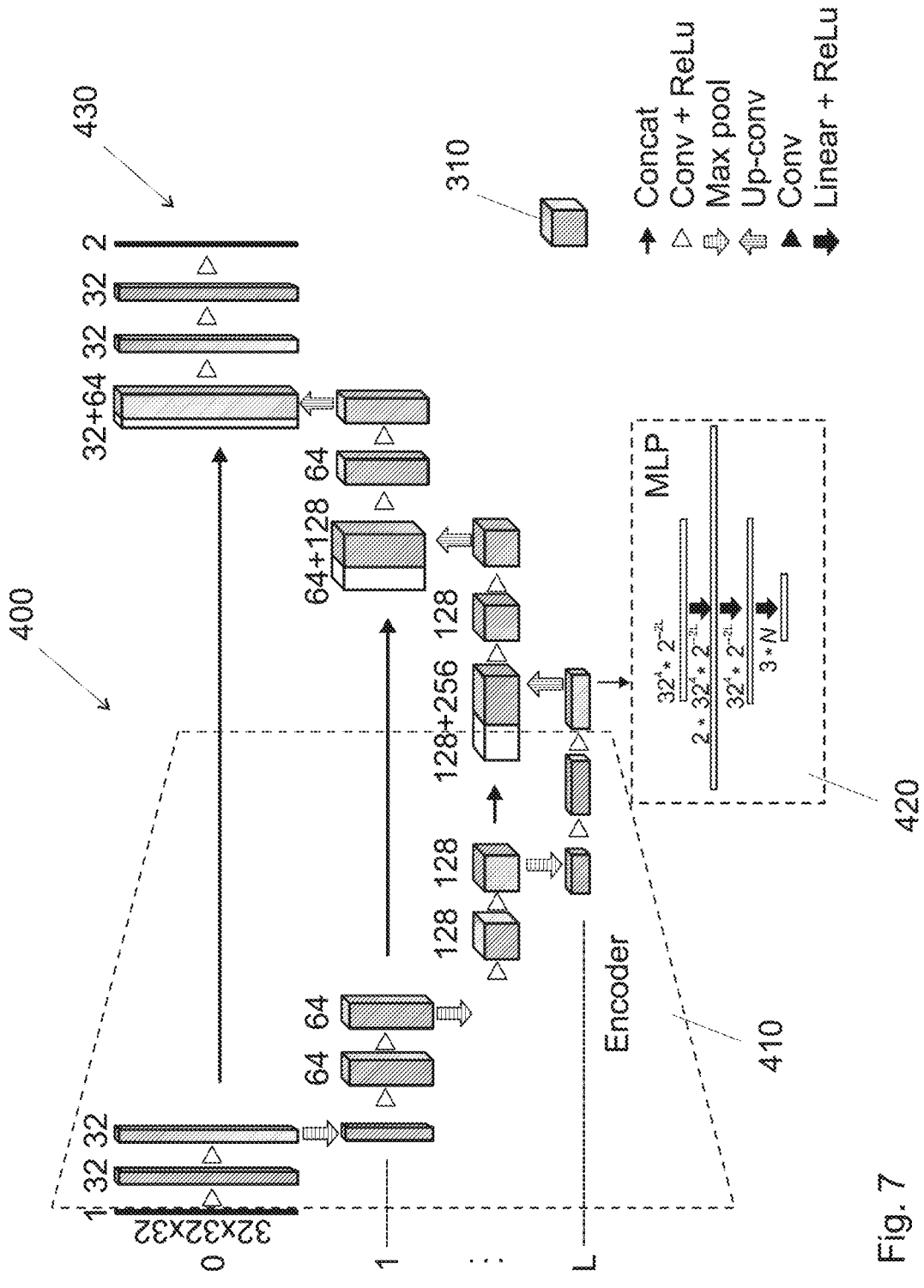
FIG. 7 is a schematic and partial representation of the real-time 3D model generating module of the system according to one embodiment of the invention.

FIG. 7 is a schematic and partial representation of a tool tracking module 400, and in particular of the deep neural network here above, of the system 100 according to one embodiment of the invention.

The deep neural network 400 of FIG. 7 comprises some elements of the 3D Unet architecture, as described in the paper 3D U-Net: Learning Dense Volumetric Segmentation from Sparse Annotation, Özgün Çiçek, Ahmed Abdulkadir, Soeren S. Lienkamp, Thomas Brox, and Olaf Ronneberger, here incorporated by reference.

As proposed in this paper, an encoder-decoder 410-430 architecture is used to extract a volumetric probability- occupancy-map of the tool 20. The reference "L" is the number of down-sampling steps. In the embodiment of FIG. 7, L=4.

As described in the paper, like the known u-net, the architecture illustrated in FIG. 7 has an analysis path with four downsampling steps and synthesis path with four upsampling steps. In the downsampling path, each down- sampling step involves two convolutions each followed by a rectified linear unit (ReLu), and finally a max pooling. In the synthesis path, each step involves an up-convolution, followed by two convolutions each followed by a ReLu. It should be noted that the number of downsampling steps, upsampling steps, convolutions and/or other functions as illustrated in FIG. 7 can be changed within the scope of the invention.

In the example of FIG. 7, the grey boxes 310 (cubes or parallelepipeds) represent feature maps. The number of channels is denoted above each feature map.

In the example of FIG. 7, the input is a 32×32×32 voxel tiles of the image with one channel. The output in the final layer is a 32×32×32 voxels in x, y, and z directions respectively. The size 32×32×32 of the voxel tile is not limitative and other sizes are possible. The higher the size, the higher the competition precision but the higher also the simulation time.

The applicant has added to the architecture proposed in this paper a unit 420 which uses the latent representation at the output of the encoder 410 so as to extract the 3D position of the centerline nodes $P_i$. The 3D position is referred to the exit 36 of the pipe 30.

In one preferred embodiment, this unit 420 is a Multi-Layer-Perceptron (MLP).

The different lines or arrows in FIG. 7 indicates the mathematical functions applied on the processed data, in particular:

Concat: Concatenation of feature maps

Conv+Relu: 3×3×3 convolution, followed by a rectified linear unit

Max pool: 2×2×2 max pooling

Up-cov: up-convolution of 2×2×2

Conv: 1×1×1 convolution

Linear+Relu: Fully connected layer followed by a rectified linear unit

Figure 8:
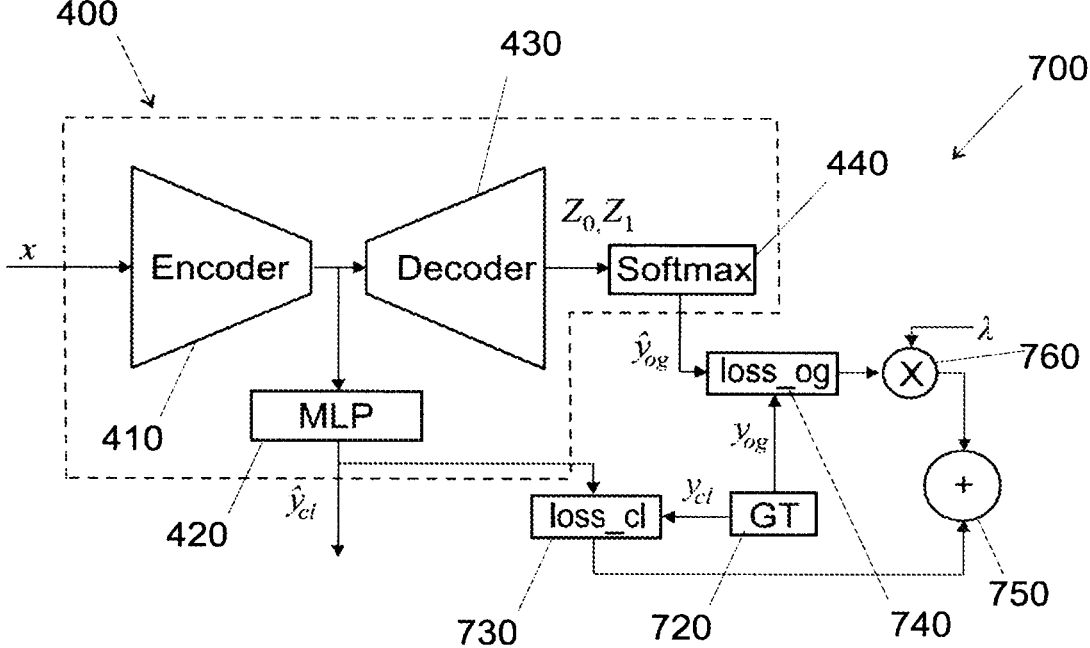
FIG. 8 is a schematic representation of the tool tracking module and of its training module, of the system according to one embodiment of the invention.

FIG. 8 is a schematic representation of the tool tracking module 400 of the system 100 according to one embodiment of the invention, along with an embodiment of its training module 700.

The ground truth (GT) unit 720 represents the desired output of the network; in one preferred embodiment, it is generated by a manual human annotation. The ground truth unit 720 comprises:

a GT occupancy grid $y_{og}$ a GT centerline $y_{ci}$.

Figure 9:
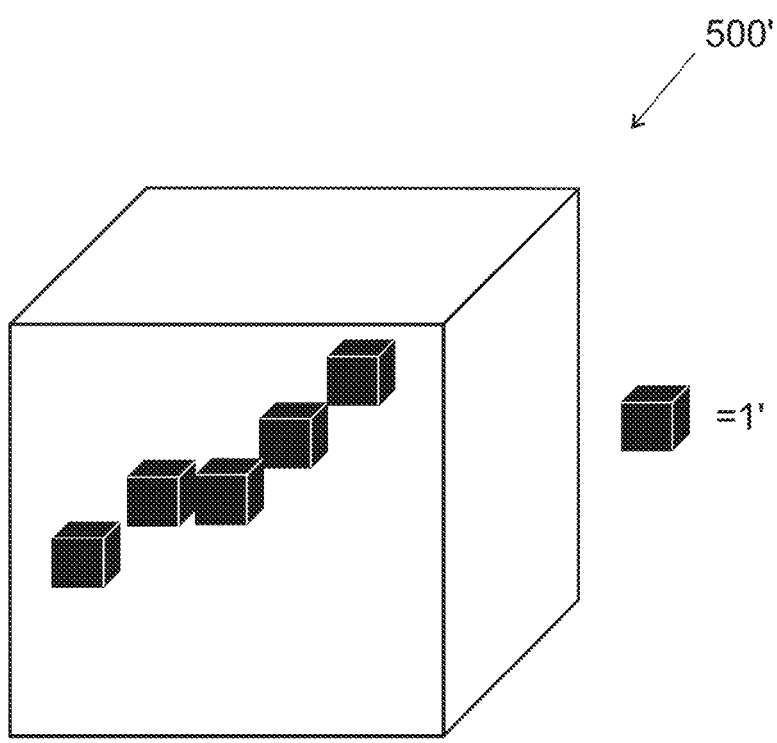
FIG. 9 illustrates an example of the ground truth (GT) occupancy grid that can be produced according to one embodiment of the method according to the invention.

As illustrated in FIG. 9, in one preferred embodiment, the GT occupancy grid $y_{og}$ (reference 500') is a binary GT occupancy grid $y_{og}$, i.e.:

$y_{og}(i,j,k)=1$, if the centerline passes through voxel $(i,j,k)$, $y_{og}(i,j,k)=0$ otherwise. (1)

In one embodiment, the GT occupancy grid 500' is of dimension 32×32×32 and the grid cells, also known as voxels, are of size 4 mm×4 mm×4 mm. Again, the dimension GT occupancy grid 500' and the size 32 of the voxel are not limitative and other dimensions or sizes are possible.

The GT centerline $y_{ci}$ is constructed by concatenating the (x,y,z) coordinates of the N centerline nodes. As illustrated in FIG. 5:

$y_{ci}=(x0,y_0,z_0,x_1,y_1,z_1, \ldots ,x_N,y_N,z_N)$ (2)

where N is the number of nodes of points of the centerline.

The input to the tool tracking module 400 is formed from a point cloud of the tool 20. In one embodiment, the 3D point cloud is computed from disparity maps obtained from the image pairs by the stereoscopic cameras 50. In one embodiment, the 3D point cloud is used to instantiate a 32×32×32 point count grid x such that x(l,j,k) is the number of cloud point within voxel (l,j,k), as depicted by FIG. 6. In one embodiment, the voxels have the same size as those of the GT occupancy grid 500'.

The tool tracking module 400 has two outputs:

a predicted (binary) occupancy grid $\hat{y}_{og}$ (reference 500 in FIG. 4), and a predicted centerline $\hat{y}_{cl}$, that is, a 3D representation of the tool 20 by N 3D points (reference 600 in FIG. 4).

In one preferred embodiment, the predicted occupancy grid $\hat{y}_{og}$ and the predicted centerline $\hat{y}_{cl}$ are in the same format as their GT counterparts $y_{og}$ and $y_{cl}$.

As shown in FIG. 8, the output of the decoder 430 is a 2-channels 3D grid, $(z_0, z_1)$. Every channel has the same format as the predicted occupancy grid $\hat{y}_{og}$.

In the embodiment of FIG. 8, the predicted occupancy grid $\hat{y}_{og}$ is obtained by applying a softmax function by using a softmax unit 440 on the output of the decoder 430:

$$\hat{y}_{og}(i, j, k) = \frac{e^{z1(i,j,k)}}{e^{z0(i,j,k)} + e^{z1(i,j,k)}} \tag{3}$$

During the learning process, in one embodiment $\hat{y}_{og}$ and $\hat{y}_{cl}$ are forced to be as similar as possible to $y_{og}$ and $y_{cl}$, by minimizing the following loss:

Loss=loss_$cl$+λ*loss_$og$ (4)

where λ is a weight and where:

loss_og is the cross entropy defined as $\Sigma-(w_1+y_{og}\log(\hat{y}_{og})+w_0*(1-y_{og})\log(1-\hat{y}_{og}))$ (5)

and loss_cl is the mean squared error over the nodes, defined as follows:

$$\sum^{N} \frac{(x_i - \hat{x}_i)^2 + (y_t - \hat{y}_t)^2 + (z_i - \hat{z}_i)^2}{3 * N} \tag{6}$$

In the embodiment of FIG. 8, the predicted probability grid $\hat{y}_{og}$ is fed also to a cross-entropy unit 740 that compares it to the GT occupancy grid $y_{og}$ observed by the stereoscopic camera(s) 50, as provided by a ground truth unit 720.

During the training of the tool tracking module 400, the predicted centerline $\hat{y}_{cl}$ as computed by the MLP 420 is fed to a regularized mean squared error unit 730 which compares it with the GT centerline $y_{cl}$ observed by the stereoscopic camera(s) 50, as provided by a ground truth unit 720.

The output of the cross-entropy unit 740 is then multiplied by a weight λ and added to the output of the regularized mean squared error unit 730, in order to compute the loss according to the formula (4).

According to an independent aspect of the invention, a Magnetic Resonance Imaging scanner or a CT scanner, connected to a computing unit of the system 100, take in real time the images of a patient during a (true) intervention. In this case, those images are used for updating a previously available (static) 3D model of organ in real time, e.g. 5 to 10 frames per second, and the updated 3D model of organ changes in real time on the display 40. According to this independent aspect of the invention, the system 100 does not comprise a pipe, as the tool is inserted by the intervention-alist in a (true) body vessel (or in a true tubular body cavity) of the patient. According to this independent aspect of the invention, the images of a portion of the tool are not taken by stereoscopic camera(s), but can be taken from the images from the Magnetic Resonance Imaging scanner or from the CT scanner. Those images allow therefore to determine the position and possibly track the position of the tool in the body of the patient. Therefore, the real-time 3D model generating unit is not necessary for this independent aspect of the invention. In one preferred embodiment, the real-time 3D model of the portion of the organ is generated by a machine-learning module.

According to one aspect of this independent aspect of the invention, instead of computing the dynamic 3D model of the end portion of the tool in real time and feeding the data into the system 100, true position data of the end portion of the tool can be downloaded during real interventions from a magnetic resonance scanner or a CT scanner, equipped with dedicated software that communicates with tools that are equipped with a tracking technology, for example based on an active tool (i.e. comprising an active tip) and/or a passive tool (i.e. a tool with MRI visible markers). These true position data of the end portion of the tool can be fed into the system 100 which enables the interventionalist to see in real time the position of the end portion of the tool in the anatomy of the patient during a true intervention.

In other words, according to one aspect of this independent aspect of the invention, the real-time 3D model generating unit is not needed. Instead the output data of this unit are replaced by position data taken from a magnetic resonance scanner or a CT scanner during real interventions. In this case, the system 100 is connected to the magnetic resonance scanner or to the CT scanner during an intervention. In this case, the magnetic resonance scanner or the CG scanner, and the tool used during the intervention are equipped with a tracking technology.

If the system 100 is connected to a magnetic resonance scanner or a CT scanner during a real intervention, a feet-head motion information can be collected in real time by the scanner and can be fed into the system 100.

According to one aspect of this independent aspect of the invention, the interventionalist can use the same system 100 during a true intervention on which the interventionalist was trained and on which the interventionalist pre-planned the intervention in a given patient.

This independent aspect of the invention allows to help the interventionalists during a true or real intervention. The previously described embodiment of the invention can be applied to this independent aspect of the invention, mutatis mutandis.

REFERENCE SIGNS USED IN THE FIGURES

10 Organ
10' (Virtual) 3D model of the organ
12 Portion of the (real) organ connected to the (real) body vessel
12' (Virtual) 3D model of the portion 12
14' (Virtual) 3D model of a zone to be treated
16' (Virtual) 3D model of a zone already treated
20 Tool
22 Handle of the tool
24 Body of the tool
26 End portion of the tool
26' Real-time 3D model of the end portion of the tool
260 Free end of the tool
260' Real-time 3D model of free end of the tool
30 Pipe
32 Entrance of the pipe
33 Foot/support of the pipe
34 Body of the pipe
36 Exit of the pipe 40 Display
40' First zone of the display
40" Second zone of the display
40'" Third zone of the display
50 Stereoscopic camera
60 Planar base
100 System
300 Grid comprising a cloud of 3D points
310 Feature map element
360 End of the pipe
400 Tool tracking module
410 Encoder
420 Multi-Layer-Perceptron (MPL)
430 Decoder
440 Softmax unit
500 Predicted occupancy grid
500' GT occupancy grid
600 Predicted 3D representation of the tool
700 Training module
720 Ground truth unit
730 Regularized mean squared error unit
740 Cross-entropy unit
750 Sum unit
760 Product unit
B Button of the display
CL Centerline
CG1 Center of gravity/center of geometry
CG2 Center of gravity/center of geometry
720/GT Ground truth unit
$\lambda$ Weight
x Input of the (second) machine learning module
$y_{cl}$ Centerline
$y_{og}$ Observed (binary) occupancy grid
T Threshold
$\hat{y}_{cl}$ Computed centerline
$\hat{y}_{og}$ Computed (binary) occupancy grid
$\hat{y}_{og.T}$ After threshold computed (binary) occupancy grid
$(x_i, y_i, z_i)$ 3D coordinates
The invention claimed is:

1. System for training an interventionalist to perform an invasive percutaneous intervention or an endoscopic intervention on an organ, by using a tool in the organ, comprises:

a pipe comprising an entrance and an exit and having a size and/or a shape equal to a body vessel or a tubular body cavity, the body vessel or the tubular body cavity being connected to the organ, wherein the exit of the pipe physically simulates or represents the exit of the vessel or of the tubular body cavity at a junction of the vessel or of the tubular body cavity with the organ;

said tool, arranged to be inserted by the interventionalist at the entrance of the pipe and to be pushed by the interventionalist through the pipe;

at least one stereoscopic camera arranged to acquire images of an end portion of the tool starting from a moment when said end portion starts emerging from the exit of the pipe;

a real-time 3D model generating unit, arranged for generating a real-time 3D model of said end portion of the tool from said images, a merging unit, arranged for merging in real-time in a common environment said real-time 3D model and a pre-computed 3D model of at least a portion of the organ;

a display for receiving data from the merging unit in order to show to the interventionalist said common environment, so that the interventionalist can see in real-time on the display where the real-time 3D model of the tool is located with respect to the pre-computed 3D model of the portion of the organ, thus making the training of the interventionalist possible.

2. System of claim 1, the 3D model of the portion of the organ being a static 3D model.

3. System of claim 1, comprising a real-time 3D model generating module, being a machine learning-based module arranged to generate said static 3D model from images from a Magnetic Resonance Imaging scanner, a CT scanner, or a device able to generate volumetric images of organs.

4. System of claim 1, comprising a tool tracking module arranged to compute and/or track in real-time a position of the end portion of the tool with regard to the exit of said pipe.

5. System of claim 1, wherein said real-time 3D model generating unit is arranged to generate from the images taken by the stereoscopic camera a cloud of 3D points that denote the position of the end portion tool with regard to the exit of said pipe.

6. System of claim 5, wherein said tracking module is arranged to use said cloud of 3D points so as to output a predicted binary occupancy grid having a value of one at a location of the tool and a value of zero at all other locations.

7. System of claim 5, wherein said tool tracking module is arranged to use said cloud of 3D points so as to output coordinates of 3D points that define a 3D position of a centerline of said tool with regard to the exit of said pipe.

8. System of claim 7, wherein said tool tracking module comprises a unit arranged to use a latent representation at an output of an encoder so as to extract the 3D position of the 3D points.

9. System of claim 8, wherein said unit is a Multi-Layer-Perceptron.

10. System of claim 8, wherein said unit is a fully connected architecture.

11. System of claim 1, wherein said 3D model of the portion of the organ comprises at least one element characterizing a lesion to be operated.

12. System of claim 1, wherein said pipe comprises a gel or a liquid simulating at least a physical property of the physical property of a physical liquid contained in the body vessel or the tubular body cavity.

13. System of claim 1, wherein said 3D model of the portion of the organ as displayed by said display is augmented by at least one target designating at least one target area of the organ that has been treated and/or that is to be treated.

14. System of claim 1, wherein said merging unit, before merging in the common environment both the real-time 3D model and the 3D model of the portion of the organ, performs calibration step so as to align a position of an end of the pipe with a position of an entry portion of the 3D model of the portion of the organ.

15. Method for training an interventionalist to an invasive percutaneous or endoscopic intervention of an organ, by using a tool in the organ comprises:

providing a pipe, said pipe comprising an entrance and an exit and having a size and/or a shape equal to a body vessel or to a tubular body cavity, the body vessel or the tubular body cavity being connected to the organ, wherein the exit of the pipe physically simulates or represents the exit of the vessel or of the tubular body cavity at a junction of the vessel or of the tubular body cavity with the organ;

inserting said tool by the interventionalist at the entrance of the pipe and pushing said tool by the interventionalist through the pipe;

acquiring by at least one stereoscopic camera images of an end portion of the tool starting from a moment when said end portion starts emerging from the exit of the pipe;

generating, by a real-time 3D model generating unit, a real-time 3D model of said end portion of the tool from said images, merging, by a merging unit, in real-time in a common environment said real-time 3D model and a pre-computed 3D model of at least a portion of the organ;

displaying said common environment on a display arranged for receiving data from the merging unit, so that the interventionalist can see in real-time on said display where the real-time 3D model of the tool is located with respect to the pre-computed 3D model of the portion of the organ, thus making the training of the interventionalist possible.

*    *    *    *    *